United States Patent [19]
Nematbakhsh et al.

[11] Patent Number: 5,781,890
[45] Date of Patent: *Jul. 14, 1998

[54] METHOD FOR MANAGING CLUSTERED MEDICAL DATA AND MEDICAL DATA FILING SYSTEM IN CLUSTERED FORM

[75] Inventors: Mohammad Ali Nematbakhsh, Anaheim, Calif.; Shinichi Tsubura, Tochigiken, Japan

[73] Assignee: Kabushiki Kaisha Toshiba, Tokyo, Japan

[*] Notice: The term of this patent shall not extend beyond the expiration date of Pat. No. 5,572,422.

[21] Appl. No.: 703,696

[22] Filed: Aug. 27, 1996

Related U.S. Application Data

[62] Division of Ser. No. 474,143, Jun. 7, 1995, Pat. No. 5,572,422, which is a continuation of Ser. No. 46,180, Apr. 14, 1993, abandoned, which is a continuation of Ser. No. 961,840, Oct. 16, 1992, abandoned.

[30] Foreign Application Priority Data

Oct. 16, 1991 [JP] Japan .................... 3-267524
Oct. 15, 1992 [JP] Japan .................... 4-277110

[51] Int. Cl.$^6$ .................... G06F 159/00
[52] U.S. Cl. .................... 705/3
[58] Field of Search .................... 395/202, 203, 395/204, 607, 615, 613, 924

[56] References Cited

U.S. PATENT DOCUMENTS

| | | | |
|---|---|---|---|
| 4,553,206 | 11/1985 | Smutek et al. | 395/612 |
| 4,945,476 | 7/1990 | Bodick et al. | 395/924 |
| 5,506,984 | 4/1996 | Miller | 395/610 |
| 5,508,502 | 4/1996 | Saito | 395/427 |
| 5,547,226 | 8/1996 | Wentworth | 283/36 |
| 5,572,422 | 11/1996 | Nematbakhsh et al. | 395/203 |

*Primary Examiner*—Donald E. McElheny, Jr.
*Attorney, Agent, or Firm*—Oblon, Spivak, McClelland, Maier & Neustadt, P.C.

[57] ABSTRACT

In a medical data managing system, a plurality of medical data are first classified based on a classification item such as sorts of medical examinations. Thereafter, the classified medical data are stored in the same optical disk, or the same clustered data recording region of the optical disk in order to effectively search/retrieve desirable medical data from a plurality of optical disks based upon the classification item covering this desirable medical data. A medical data managing system comprises: a unit for sequentially acquiring a plurality of medical data about a biological body under medical examination; a unit for classifying the plurality of medical data based upon at least one of medical classification items to obtain a plurality of classified medical data; and a unit for sequentially storing the plurality of classified medical data into a plurality of data storage mediums in such a manner that the plurality of classified medical data belonging to the same classification item are stored in the same data storage medium.

20 Claims, 12 Drawing Sheets

| CLUSTER NO. | OPTICAL DISK NO. | EXAMINATION TERM |
|---|---|---|
| 1 | 10 | 1991.10.1 ~ 1991.12.31 |
| | 11 | |
| | 12 | |
| 2 | 13 | 1992.1.1 ~ 1992.3.31 |
| | 14 | |
| | 15 | |
| 3 | 16 | 1992.4.1 ~ 1992.6.30 |
| | 17 | |
| | 18 | |
| 4 | 19 | 1992.7.1 ~ 1992.9.30 |
| | 20 | |
| | 21 | |

FIG.5

| PATIENT NAME | EXAMINATION | | | RECORDED OD |
| --- | --- | --- | --- | --- |
| | DATE | DIAG. | SHEET | |
| TSUBURA | 1991. 10. 11 | CHEST X-RAY | 5 | 10 |
| | 15 | C T | 30 | 10 |
| | 29 | M R I | 25 | 10 |
| | 12. 17 | CHEST X-RAY | 3 | 10 |
| | 1992. 1. 15 | C T | 10 | 10 |
| | 3. 20 | X-RAY | 5 | 10 |
| | 5. 17 | X-RAY | 3 | 17 |
| | 7. 3 | X RAY | 2 | 17 |
| | 9. 24 | X RAY | 3 | 17 |
| TARO | 1991. 11. 10 | N M | 10 | 15 |
| | 11. 20 | C T | 50 | 15 |
| | 11. 25 | M R I | 30 | 15 |
| HANAKO | 1991. 11. 3 | CHEST X-RAY | 30 | 13 |
| | 11. 10 | C T | 30 | 13 |
| A | 1991. 12. 5 | C T | 50 | 16 |
| B | 1991. 10. 19 | X-RAY | 3 | 11 |
| C | 1991. 11. 7 | M R I | 20 | 14 |
| D | 1991. 10. 22 | X-RAY | 5 | 12 |
| E | 1992. 4. 28 | C T | 20 | 18 |

FIG. 8

| PATIENT NAME | EXAMINATION | | | RECORDED OD |
| --- | --- | --- | --- | --- |
| | DATE | DIAG. | SHEET | |
| TSUBURA | 1991. 10. 11 | CHEST X-RAY | 5 | 10 |
| | 15 | C T | 30 | 10 |
| | 29 | M R I | 25 | 10 |
| | 12. 17 | CHEST X-RAY | 3 | 10 |
| | 1992. 1. 15 | C T | 10 | 13 |
| | 3. 20 | X-RAY | 5 | 13 |
| | 5. 17 | X-RAY | 3 | 16 |
| | 7. 3 | X RAY | 2 | 19 |
| | 9. 24 | X RAY | 3 | 19 |
| TARO | 1991. 11. 10 | N M | 10 | 12 |
| | 11. 20 | C T | 50 | 12 |
| | 11. 25 | M R I | 30 | 12 |
| HANAKO | 1991. 11. 3 | CHEST X-RAY | 30 | 11 |
| | 11. 10 | C T | 30 | 11 |
| A | 1991. 12. 5 | C T | 50 | 11 |
| B | 1991. 10. 19 | X-RAY | 3 | 11 |
| C | 1991. 11. 7 | M R I | 20 | 12 |
| D | 1991. 10. 22 | X-RAY | 5 | 12 |
| E | 1992. 4. 28 | C T | 20 | 17 |

FIG.9

| CLUSTER NO. | OPTICAL DISK NO. | EXAMINATION TERM |
|---|---|---|
| 1 | 10<br>11<br>12 | 1991.10.1 ~ 1991.12.31 |
| 2 | 13<br>14<br>15 | 1992.1.1 ~ 1992.3.31 |
| 3 | 16<br>17<br>18 | 1992.4.1 ~ 1992.6.30 |
| 4 | 19<br>20<br>21 | 1992.7.1 ~ 1992.9.30 |

FIG.10

| OPTICAL DISK NO. | SLOT NO. |
|---|---|
| 10 | 3 |
| 11 | 5 |
| 12 | 7 |
| 13 | 6 |
| 14 | 4 |
| 15 | 8 |
| 16 | 9 |
| 17 | 12 |
| 18 | 11 |
| 19 | 10 |
| 20 | 13 |
| 21 | 14 |

FIG. 11

| CLUSTER NO. | EXAMINATION TERM | PATIENT NAME | EXAMINATION DATE | EXAMINATION DIAG. | SHEET | RECORDED OD |
|---|---|---|---|---|---|---|
| 1 | 1991.10.1 ~ 1991.12.31 | TSUBURA | 1991.10.11 | CHEST X-RAY | 5 | 10 |
| | | " | 15 | CT | 30 | 10 |
| | | " | 29 | MRI | 25 | 10 |
| | | TARO | 12.17 | CHEST X-RAY | 3 | 10 |
| | | " | 1991.11.10 | NM | 10 | 12 |
| | | " | 20 | CT | 50 | 12 |
| | | HANAKO | 25 | MRI | 30 | 12 |
| | | " | 1991.11.3 | CHEST X-RAY | 30 | 11 |
| | | A | 11.10 | CT | 30 | 11 |
| | | B | 1991.12.5 | CT | 50 | 11 |
| | | C | 1991.10.19 | X-RAY | 3 | 12 |
| | | D | 1991.11.7 | MRI | 20 | 12 |
| | | " | 1991.10.22 | X-RAY | 5 | 12 |
| 2 | 1992.1.1 ~ 1992.3.31 | TSUBURA | 1992.1.15 | CT | 10 | 13 |
| | | " | 3.20 | X-RAY | 5 | 13 |
| 3 | 1992.4.1 ~ 1992.6.30 | TSUBURA E | 1992.5.17 | X-RAY | 3 | 16 |
| | | " | 1992.4.28 | CT | 20 | 17 |
| 4 | 1992.7.1 ~ 1992.9.30 | TSUBURA | 1992.7.3 | X-RAY | 2 | 19 |
| | | " | 9.24 | X-RAY | 3 | 19 |

METHOD FOR MANAGING CLUSTERED MEDICAL DATA AND MEDICAL DATA FILING SYSTEM IN CLUSTERED FORM

This is a division of application Ser. No. 08/474,143 filed on Jun. 7, 1995 now U.S. Pat. No. 5,572,422, which is a continuation of Ser. No. 08/046,180, filed on Apr. 14, 1993, now abandoned, which is a Continuation of Ser. No. 07/961,840 filed on Oct. 16, 1992, abandoned.

BACKGROUND OF THE INVENTION

1. Field of the Invention

The present invention generally relates to a medical data managing method and a medical data filing system. More specifically, the present invention is directed to a method and an apparatus capable of managing and filing medical data in a clustered form on a recording medium, e.g., optical disks.

2. Description of the Prior Art

In various medical electronics apparatuses such as an X-ray CT (computerized tomographic) imaging apparatus and an MR (magnetic resonance) imaging apparatus, a plurality of imaging data are acquired and time-sequentially recorded on recording mediums, e.g., optical disks, and at any time, are searched/retrieved from these recording mediums for medically diagnostic purposes.

More specifically, in accordance with one conventional data filing system, medical data such as CT image data acquired by imaging a biological body under medical examination are time-sequentially stored/recorded in a serial form on each of plural optical disks in such a manner that after one optical disk is filled with a series of medical data, a subsequent optical disk is used to record another series of medical data in a serial form. In other words, the medical data are merely, time-sequentially stored in the optical disk without classifying or categorizing contents of these medical data.

Referring now to FIG. 1, an overall arrangement of one conventional medical data managing system will be described. In this drawing, medical data is inputted from a medical data input unit 1 into a data file control unit 2. Then, a series of medical data are time-sequentially recorded on a relevant optical disk (not shown in detail) employed in an optical disk autochanger 3 under control of the data file control unit 2. After these medical data have been time-sequentially stored in such a serial form on the plural optical disks, data search/retrieval operations are carried out by a medical data search/retrieve unit 4 through the data file control unit 2. In this conventional medical data managing system, there are many possibilities to load a desirable optical disk on the disk drive of the optical disk autochanger 3. That is, a large number of optical disks must be frequently selected to be loaded on the disk drive in order to search/retrieve desired medical data from the relevant optical disks. For instance, in case that after one medical data has been searched/retrieved from one recording region of an optical disk, another medical data is searched/retrieved from another recording region of the same optical disk, an overall search/retrieval time requires only several hundreds milliseconds. However, if such a data search/retrieve operation is performed by replacing one optical disk with another optical disk on the disk drive by using the mechanical replacing device, an overall search/retrieval time amounts to several tens seconds. Accordingly, a throughput of this conventional medical data managing system becomes rather low.

A more effective medical data managing system is required in the medical electronic field.

SUMMARY OF THE INVENTION

The present invention has been made to realize such a highly effective medical data managing system, and therefore, has an object to provide medical data managing method/system capable of managing medical data in accordance with a classification so as to effectively search/retrieve a large number of classified medical data.

Another object of the present invention is to provide medical data recording method/system capable of storing a large quantity of medical data in a cluster form into a recording medium.

To achieve the objects, according to one aspect of the present invention, a medical data managing method comprises the steps of:

sequentially acquiring a plurality of medical data about a biological body under medical examination;

classifying said plurality of medical data based upon at least one of medical classification items to obtain a plurality of classified medical data; and sequentially storing said plurality of classified medical data into a plurality of data storage mediums ($22_1$, $22_2$, - - - , $22_n$) in such a manner that said plurality of classified medical data belonging to the same classification item are stored in the same data storage medium ($22_1$, - - - , $22_n$).

Further, according another aspect of the present invention, a medical data managing system (100:200) comprises:

means (50-1) for sequentially acquiring a plurality of medical data about a biological body under medical examination;

means (50-6) for classifying said plurality of medical data based upon at least one of medical classification items to obtain a plurality of classified medical data; and means (50-5:50-9:50-10) for sequentially storing said plurality of classified medical data into a plurality of data storage mediums ($22_1$, $22_2$, - - - , $22_n$) in such a manner that said plurality of classified medical data belonging to the same classification item are stored in the same data storage medium ($22_1$, $22_2$, - - - , $22_n$).

Also, according to a still aspect of the present invention, a medical data filing system (100:200) comprises:

medical data input means (50-1) for inputting a plurality of medical data about a biological body under medical examination;

a plurality of storage mediums ($22_1$:$22_n$) capable of storing said medical data;

data information recognizing means (50-4) for recognizing medical data information attached to said medical data to derive data recognition information;

storage medium managing means (50-6) for classifying said plurality of medical data based upon at least one of classification items covering said data recognition information; and file system managing means (50-5:50-5A) for filing said classified medical data in said storage mediums ($22_1$:$22_n$) in such a manner that said classified medical data belonging to the same classification item are filed into the same data storage medium, whereby desirable medical data is searched/retrieved from the data storage mediums based upon the classification item covering the data recognition information of said desirable medical data.

BRIEF DESCRIPTION OF THE DRAWINGS

For a better understanding of the present invention, reference is made of the following descriptions in conjunction with the accompanying drawings, in which.

3

Figure 1:
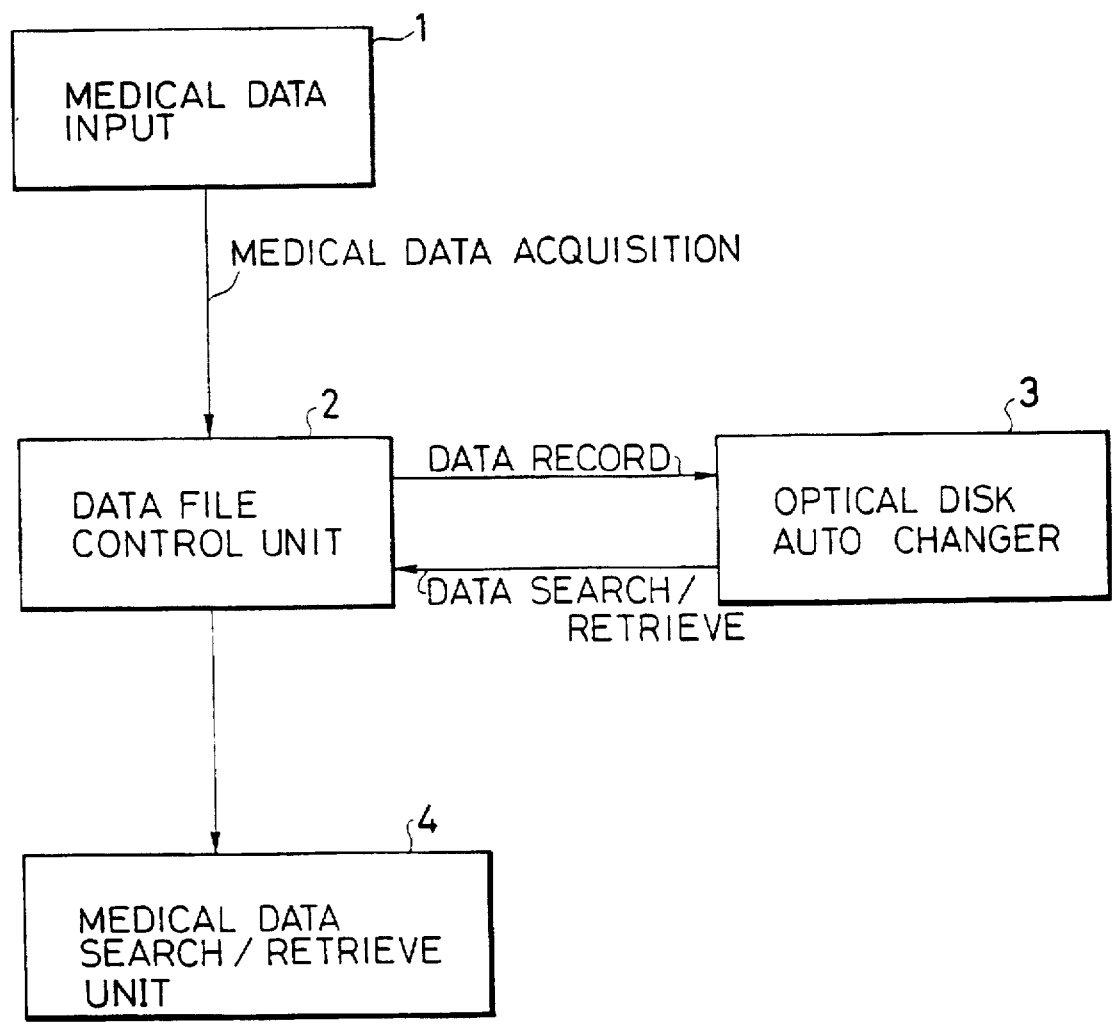
FIG. 1 schematically illustrates the arrangement of the conventional medical data managing system.
Figure 2:
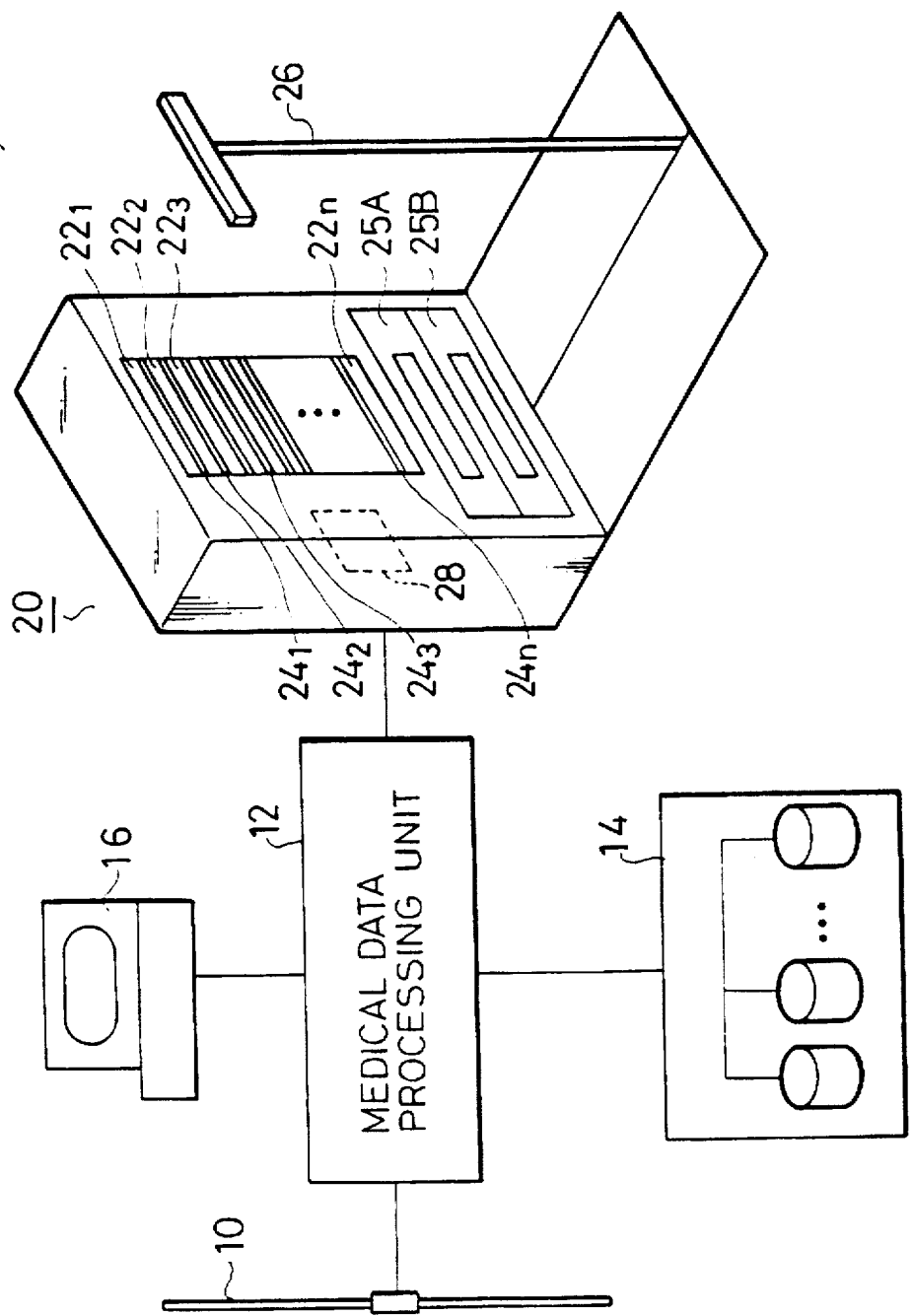
Figure 3:
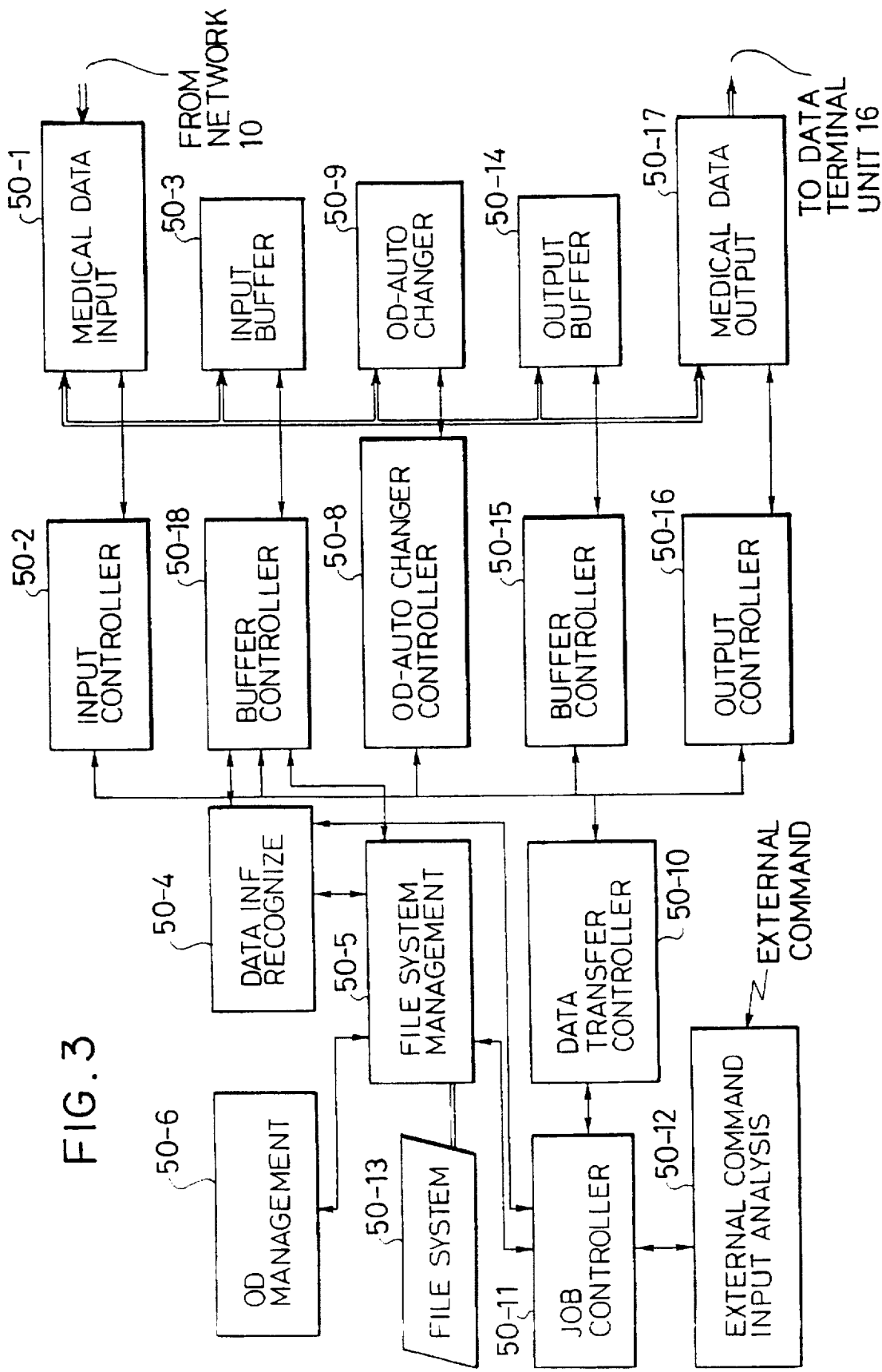
Figure 4A:
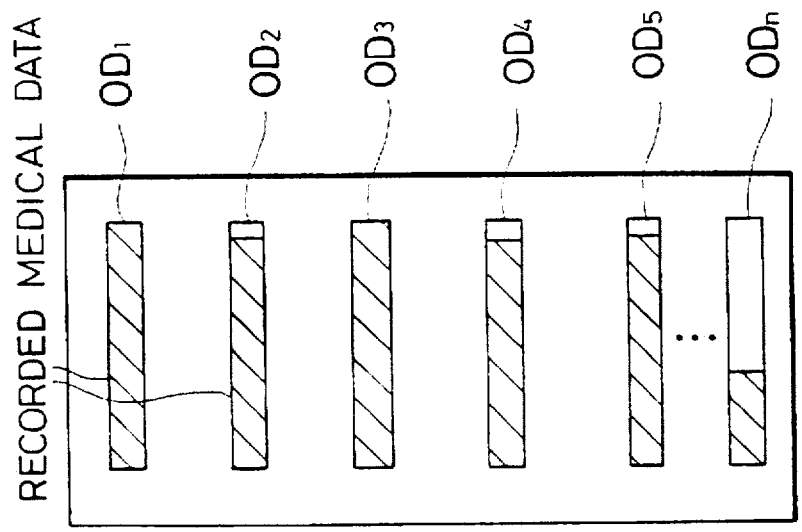
Figure 4B:
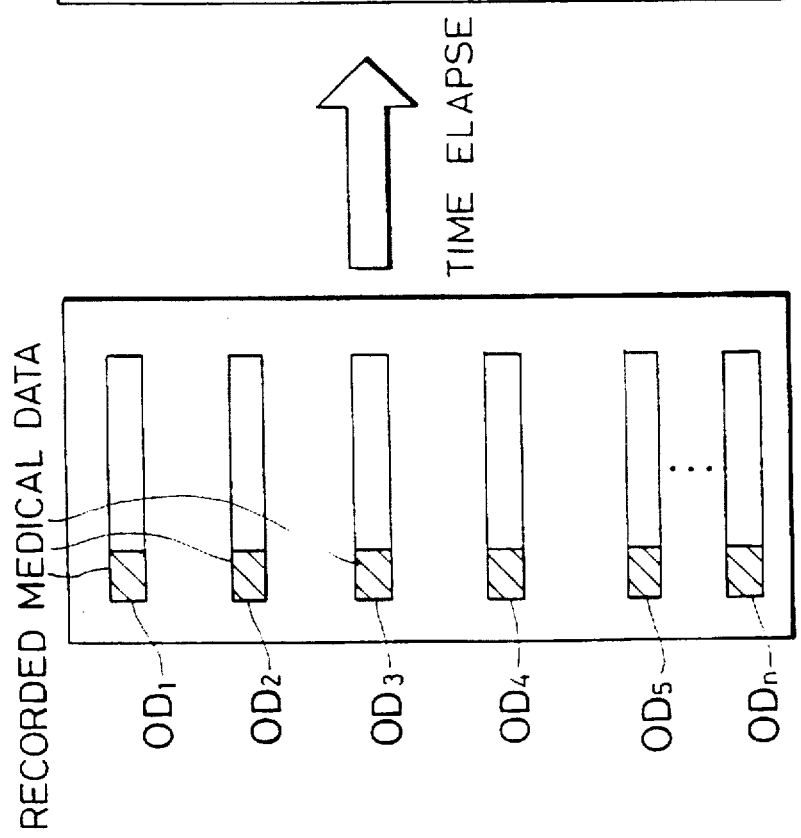
Figure 6:
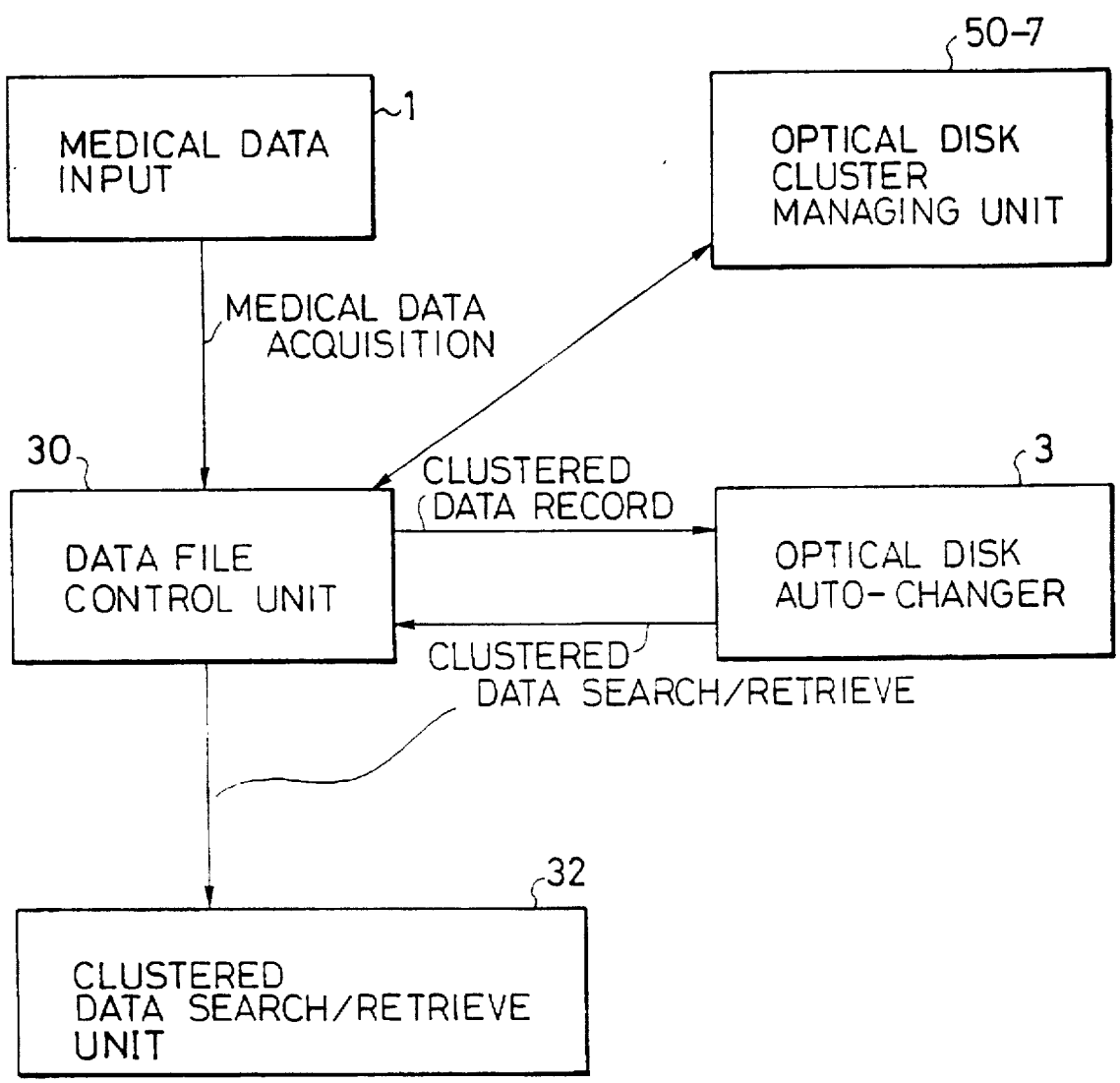
Figure 7:
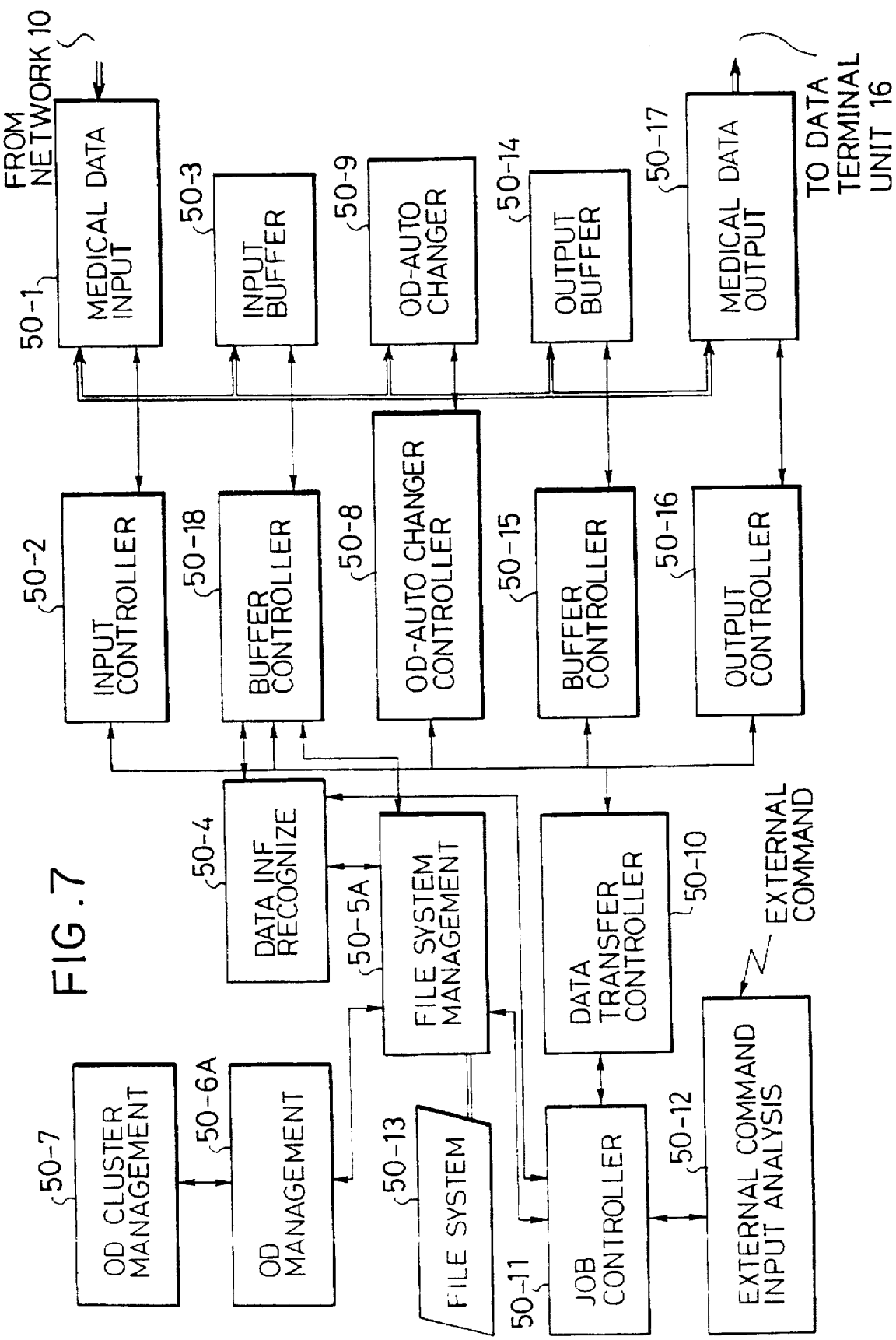
Figure 12:
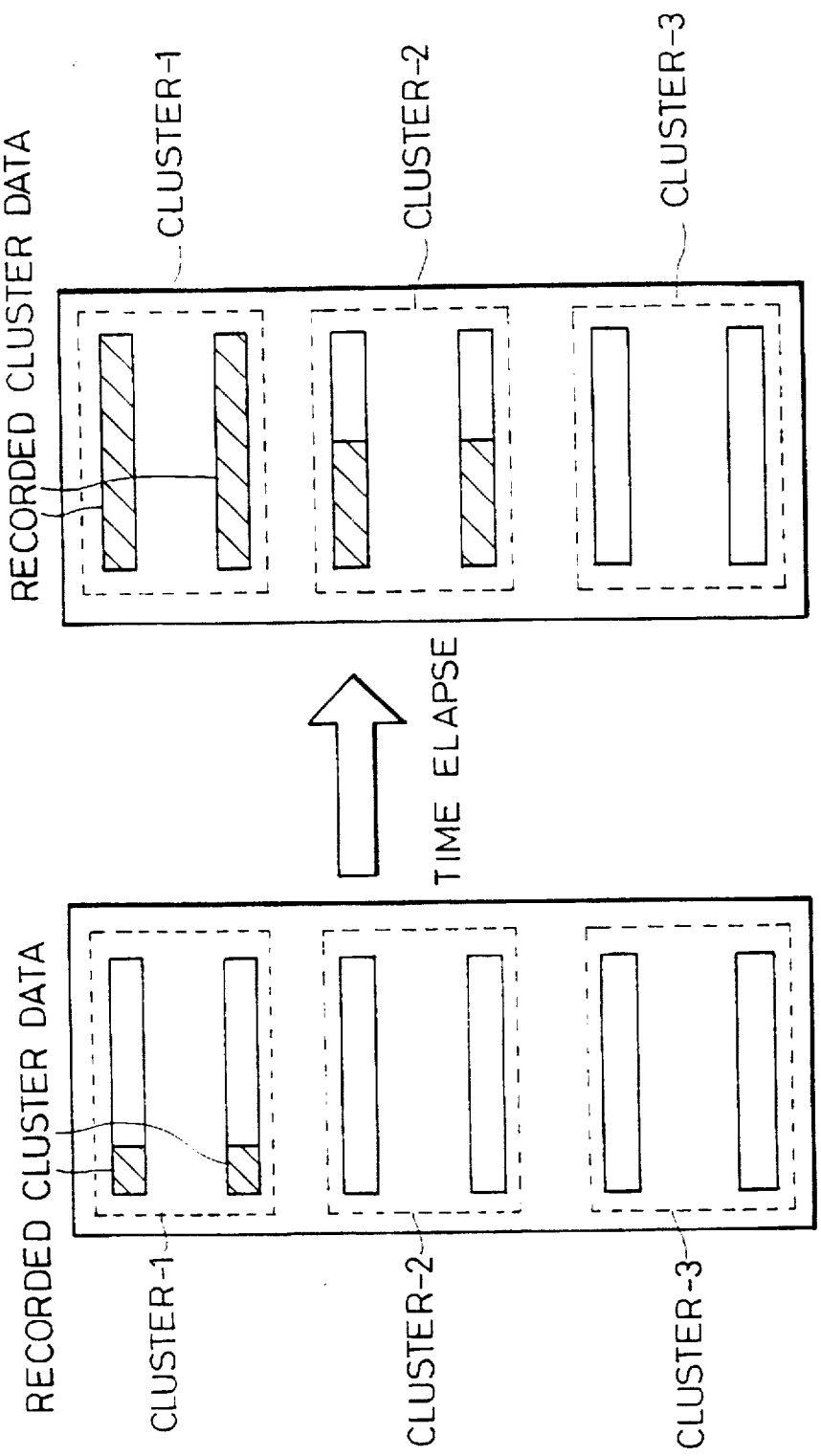
Figure 13:
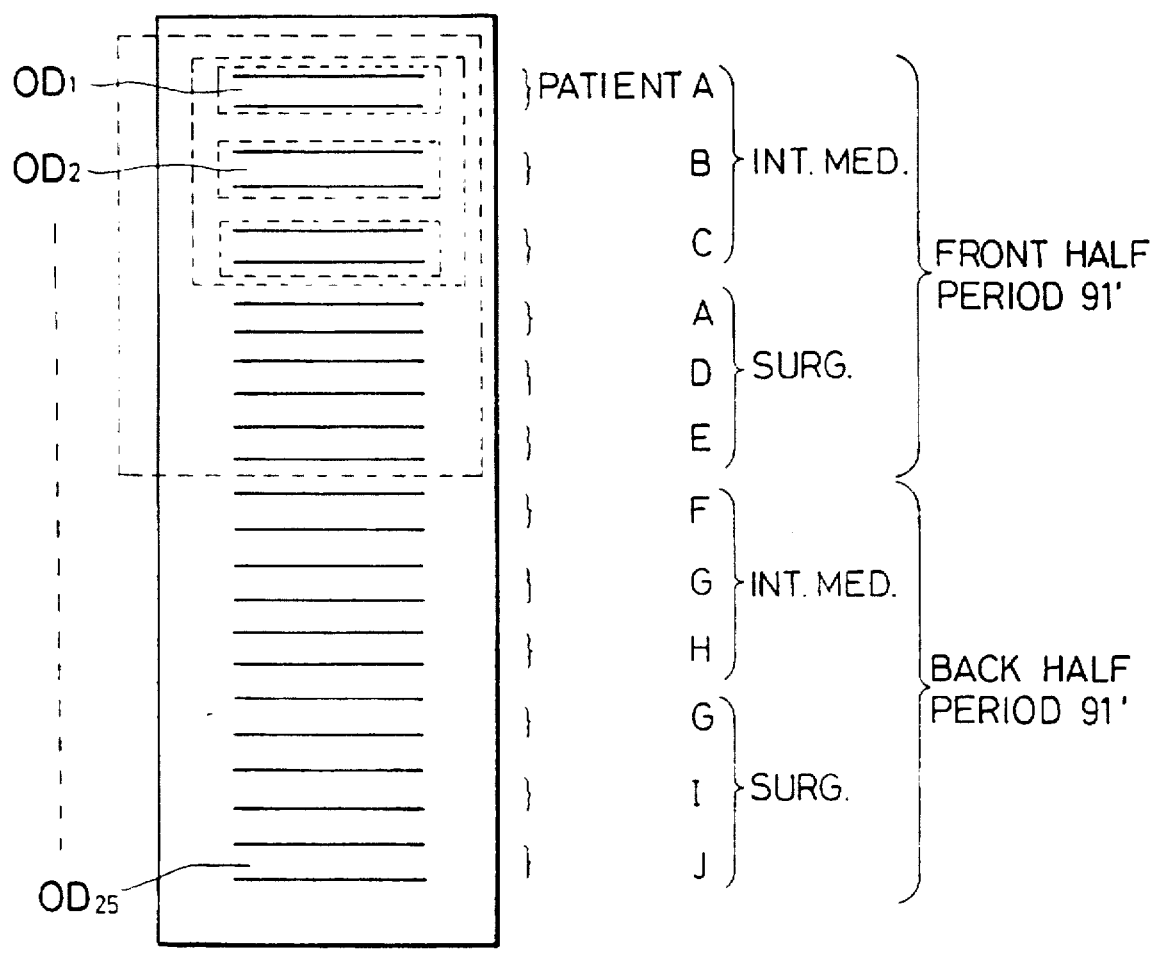

FIG. 2 schematically represents an overall arrangement of a medical data managing system 100 according to a first preferred embodiment of the present invention;

FIG. 3 is a schematic block diagram for showing a circuit arrangement of the first medical data managing system 100 shown in FIG. 2;

FIGS. 4A and 4B pictorially explain conditions of the medical data recorded on the optical disks stored in the first medical data managing system 100;

FIG. 5 represents a file management table employed in the first medical data managing system 100;

FIG. 6 represents a conceptional diagram of an arrangement of another medical data managing system 200 according to a second preferred embodiment of the present invention;

FIG. 7 is a schematic block diagram for indicating a circuit arrangement of the second medical data managing system 200 shown in FIG. 6;

FIG. 8 indicates a file management table employed in the second medical managing system 200;

FIG. 9 shows a cluster management table employed in the second medical data managing system 200;

FIG. 10 represents a slot management table employed in the second medical data managing system 200;

FIG. 11 indicates a cluster/file management table employed in the second medical data managing system 200;

FIGS. 12A and 12B pictorially explain conditions of the clustered medical data recorded on the optical disks in the second medical data managing system 200; and FIG. 13 schematically represents contents of clustered medical data recorded on optical disks according to a third preferred embodiment of the present invention.

DETAILED DESCRIPTION OF THE PREFERRED EMBODIMENTS

OVERALL CONSTRUCTION OF FIRST MEDICAL DATA MANAGING SYSTEM

In FIG. 2, there is shown an overall construction of a medical data managing system 100 according to a first preferred embodiment of the present invention.

Medical data such as X-ray CT (computerized tomographic) imaging data and MR (magnetic resonance) imaging data related to a biological body under medical examination (not shown in detail), are acquired by proper medical electronics apparatuses, e.g., X-ray CT imaging apparatus (not shown). These medical data are supplied via a network 10 to a medical data processing unit 12. The medical data are temporarily stored into a magnetic disk unit 14, and also are stored in accordance with a classification (will be discussed later) into a plurality of optical disks $22_1, - - - , 22_n$ ("n" being an integer greater than 2) employed in an optical disk autochanger 20. A data terminal unit 16 is coupled to the medical data processing unit 12.

In the optical disk autochanger 20, these optical disks $22_1, - - - , 22_n$ are stored in a plurality of slots $24_1, - - - , 24_n$. Two disk drives 25A and 25B are provided under these slots $24_1, - - - , 24_n$. Then, the selected optical disks are automatically loaded in conjunction with an automatic changing arm 26 for a disk replacement purpose under control of a controller 28.

As a major feature of this first medical data managing system 100, a large number of medical data are classified based on the below-mentioned 5 items, and thereafter, the classified medical data are recorded on the relevant optical disks $22_1, - - - , 22_n$.

4

Classification of Medical Data

1) The same medical examination data are stored into the same optical disk, or disks 22. (i.e., same clustered recording region of the disk)

2) The medical data about the same patient are stored into the same optical disk, or disks 22.

3) The medical data derived from the same modality are stored in the same optical disk, or disks 22.

4) The medical data belonging to the same diagnostic department are stored in the same optical disk, or disks 22.

5) The medical data are successively stored into an empty (unrecorded) optical disk, or disks 22.

CIRCUIT ARRANGEMENT OF FIRST MEDICAL DATA MANAGING SYSTEM

FIG. 3 schematically shows a circuit arrangement of the first medical data managing system 100. This circuit arrangement corresponds to the above-described medical data processing unit 12 and control unit 28 shown in FIG. 2, and can classify a plurality of medical data in accordance with the previously explained classification items 1) to 5) (will be described more in detail).

For a better understanding of an overall operation of the first medical data managing system 100, three typical operations (data recording, searching and retrieving operations) thereof will now be separately described:

MEDICAL DATA RECORDING OPERATION

In FIG. 3, medical data are inputted from the network (see FIG. 2), or other medium (not shown in detail) via a medical data input unit 50-1 to an input buffer 50-3 under control of an input controller 50-2. It should be noted that this medical data input unit 50-1 involves other data transfer devices connected to an internal bus.

The medical data entered into the input buffer 50-2 is format-converted under control or a buffer controller 5-18, if required. Accordingly, information required to constitute a file system is derived from the inputted medical data, and thereafter sent to a file system managing circuit 50-5 by which these medical data are numbered. Then, the numbered medical data are to be managed.

In an optical disk managing circuit 50-6, a selection is made of the optical disk 22 into which the classified medical data area stored.

To record the medical data on the selected optical disk $22_1, - - - ,$ or $22_n$, this optical disk 22 is transported from the slot 24 to either the first drive 25A or the second drive 25B under control of an OD-autochanger controller 50-8 in the optical disk autochanger 50-9. Thereafter, the medical data inputted from the input buffer 50-3 is written into the selected optical disk 22. Furthermore, the information about the record number or the like is registered in the file system managing circuit 50-5.

It should be noted that a series of the above-described operations is achieved by way of a data transfer controller 50-10 for controlling the respective device controllers 50-2, 50-4, 50-18; and also a job controller 50-11 for controlling the file system managing circuit 50-5, the data information recognizing circuit 50-4. An external command input analyzing unit 50-12 is connected to this job controller 50-11 for accepting user's commands derived from either the communication network, or the input terminal to analyze these commands, so that the analyzed commands are entered into this job controller 50-11.

As previously explained in detail, since a series of medical data is classified and thereafter the classified medical data are stored into the same optical disks $22_1, - - - , 22_n$, easy and quick medical data managements such as the search operation can be realized. Moreover, even after a certain time elapses, most of optical disks "$OD_d$", - - - "$OD_n$" are filled with the classified medical data under equal recording conditions as illustrated in FIGS. 4A and 4B.

MEDICAL DATA SEARCHING OPERATION

When key information (namely, index information) required for a search operation is given via a the external command input analyzing unit 50-12, the file system 50-13 is searched by the file system managing circuit 50-5 and this key information is transferred from the external command input analyzing unit 50-12 to this file system 50-13. As a result, the desired medical data is searched from the relevant optical disk 22 based upon the key (index) information under control of the file system 50-13 and the file system managing circuit 50-5.

It should be noted that the file system 50-13 contains an optical disk file management table, the contents of which are represented in FIG. 5.

MEDICAL DATA RETRIEVING OPERATION

Similarly, when a designation is made of medial data wanted to be outputted, for example, X-ray CT image data of a patient by operating the external command input analyzing unit 50-12, both of the index (key) information about the relevant optical disk 22 containing this medical data, and the positional information (record number) of this medical data within the relevant optical disk 22 are acquired via the file system managing circuit 50-5 and the optical disk managing circuit 50-6 by the job controller 50-11. Subsequently, the designated optical disk $22_1$, - - -, or $22_n$ is transported from the corresponding slot $24_1$, - - -, or $24_n$ in the optical disk autochanger 50-9 via the buffer controller 50-8 under control of the data transfer controller 50-10. Then, this desired medical data is read out from the designated optical disk and supplied to the output buffer 50-14. From this output buffer 50-14, the read medical data is format-converted in the buffer controller 5-15. Finally, the format-converted desirable medical data is outputted from the medical data output unit 50-17 under control of the output controller 50-16.

ADVANTAGES OF FIRST MEDICAL DATA MANAGING SYSTEM

The above-described first medical data managing system 100 has various advantages. For the sake of easy understanding of these advantages, a description will now be made of various merits in recording medical data on an optical disk, or disks.

As previously described, when medical data are recorded on a optical disk, the medical data are first classified in accordance with the below-mentioned condition (a single condition, or combined conditions). Then, the medical data having the same classification should be recorded on the same optical disk.

CLASSIFICATION CONDITIONS

A). Memory Capacity of Optical Disk

A-1). Empty Memory Capacity

To record the medial data with a minimum classified data unit with respect to an image unit or an examination unit on the same optical disk 22, a selection is made of such an optical disk $22_1$, $22_2$, - - -, or $22_n$ whose empty memory space (capacity) is equal to, or greater than the minimum classified data unit (namely, medical data allocation).

A-2). Memory Capacity Equalization

A selection is made of an optical disk whose empty memory space is minimum among other optical disks. Then, the resultant memory capacities of the respective optical disks can be equalized with each other.

B). User's Data Classification

A classification is carried out with regard to either attributive information or searching key information given to each medical data. The attributive information corresponds to the information constituting the file system 50-13 and the information derived from the data information recognizing circuit 50-4.

As the attributive/searching key information, there are provided:

medical examinations, patients, modalities (diagnostic apparatuses, examination apparatuses), diagnostic departments, doctors, degrees of importance, official reports/unofficial reports, sorts of medical data (reports, images, cardiograms) etc.

As a consequence, in accordance with the first medical data managing system 100, the number of optical disk replacements for the disk drives 25A and 25B may be reduced as much as possible, so that the throughput of this managing system 100 can be improved.

BASIC IDEA OF SECOND MEDICAL DATA MANAGING SYSTEM

Before describing a basic idea of another medical data managing system according to a second preferred embodiment of the present invention, essential usage of a medical data filing system equipped with an optical disk autochanger will be explained in detail.

The medical data filing system equipped with the optical disk autochanger mainly aims to search as well as retrieve medical data. In other words, the medical data filing operation is executed in order to search/retrieve the desirable medical data. Under such a specific circumstance in the medical electronics field, even when one optical disk is completely filled with the classified medical data, this optical disk filled with full data is not immediately replaced by another empty optical disk, namely it is not brought into the offline condition. To diagnose any changes in disease conditions of a patient, such an optical disk filled with the full data must be maintained or stored with the corresponding slot of the optical disk autochanger for, a long temporal term, e.g., 3 months to 2 years. In particular, 3-month storage of such a data-filled optical disk is required in order to judge whether a patient becomes a chronic disease, or an acute disease in view of medical diagnosis.

However, in accordance with the above-described first medical data managing system 100, as shown in FIGS. 4A and 4B, the most optical disks $OD_1$, - - - , $OD_n$ may be completely filled with the classified medical data at the substantially same time, taking account of a long temporal term (see FIG. 4B). Since these data-filled optical disks must be kept in the slots for such a long temporal term (1 to 2 years), no new medical data can be recorded during this long temporal term. Moreover, when these data-filled optical disks are allowed to be replaced by new (unrecorded) optical disks, these old disks are entirely released from the slots (i.e., offline conditions), so that there is no possibility to access medical data stored in these old optical disks under online state, resulting in difficulties of diagnose, and also medical data management.

To improve the above-described first medical data managing system 100, the second medical data managing system 200 has been invented by introducing a data clustering idea (will be discussed more in derail) in addition to the above-explained data classification.

Referring now to FIG. 6, a basic idea (namely, data clustering process) of the second medical data managing system 200 will be described.

In FIG. 5, a series of medical data are supplied from the medical data input unit 1 into a data file control unit 30. In this data file control unit 30, these medical data are grouped, or clustered under control of an optical disk cluster managing unit 50-7 (will be described later). The grouped or clustered medical data are successively recorded on the corresponding optical disk, or disks within the optical disk autochanger 3. When either a searching operation, or a retrieving operation is carried out, desirable clustered data is searched/retrieved by a clustered data search/retrieve unit 32.

The above-described data clustering idea is achieved as follows: that is, a data recording term is newly employed as the data recording conditions, namely the above-explained data classification conditions A) and B) of the first medical data managing system 100. For instance, assuming now that 3 months are set as the data recording term (cluster condition), a series of medical data are classified or grouped during this data recording term based upon the classification conditions A) and B) (will be discussed more in detail).

CIRCUIT ARRANGEMENT OF SECOND MEDICAL DATA MANAGING SYSTEM

FIG. 7 is a schematic circuit block diagram of the second medical data managing system 200.

As apparent from a comparison between FIG. 7 and FIG. 3, only three circuits of the second medical data managing system 200 are different from the overall circuit of the first medical data managing system 100, namely the above-described optical disk cluster managing circuit 50-7, an optical disk managing circuit 50-6A and a file system managing circuit 50-5A.

Similarly, three typical operations (data recording/ searching/retrieving operations) of the second data managing system 200 will now be successively described in detail in conjunction with FIGS. 7 to 11. FIG. 8 shows a content of an optical disk file management table stored in the file system 50-13. FIG. 9 represents a content of an optical disk cluster management table stored in the optical disk cluster managing circuit 50-7. FIG. 10 indicates a content of an optical disk slot management table stored in the optical disk autochanger controller 50-8. FIG. 11 denotes a content of an optical disk cluster file management table stored in the optical disk cluster managing circuit 50-7.

CLUSTERED DATA RECORDING OPERATION

In FIG. 7, a series of medical data are similarly inputted from the network 10 (see FIG. 2), or other medium (not shown in detail) via a medical data input unit 50-1 to an input buffer 50-3 under control of an input controller 50-2. It should be noted that this medical data input unit 50-1 involves other data transfer devices connected to an internal bus.

The medical data entered into the input buffer 50-2 is format-converted under control of a buffer controller 5-18, if required. Accordingly, information required to constitute a file system is derived from the inputted medical data, and thereafter set to a file system managing circuit 50-5A by which these medical data are numbered. Then, the numbered medical data are to be managed.

In an optical disk managing circuit 50-6A, a selection is made of the optical disk 22 into which the clustered medical data are stored. That is, the medical data are classified based on the above-described classification items and also the cluster condition, e.g., 3-month recording term.

To record the clustered medical data on the selected optical disk $22_1$, - - - , or $22_n$, this optical disk 22 is transported from the slot 24 to either the first drive 25A or the second drive 25B under control of an OD-autochanger controller 50-8 in the optical disk autochanger 50-9. Thereafter, the medical data inputted from the input buffer 50-3 is written into the selected optical disk 22 as the clustered medical data. Furthermore, the information about the record number or the like is registered in the file system managing circuit 50-5A (see file management table of FIG. 8).

It should be noted that a series of the above-described operation is achieved by way of a data transfer controller 50-10 for controlling the respective device controllers 50-2, 50-4, 50-16: and also a job controller 50-11 for controlling the file system managing circuit 50-5A, the data information recognizing circuit 50-4. An external command input analyzing unit 50-12 is connected to this job controller 50-11 for accepting user's commands derived from either the communication network, or the input terminal to analyze these commands, so that the analyzed commands are entered into this job controller 50-11.

CLUSTERED DATA SEARCHING OPERATION

When key information (namely, index information) required for a search operation is given via the external command input analyzing unit 50-12, the file system 50-13 is searched by the file system managing circuit 50-5A in conjunction with the optical disk file management table of FIG. 8 and this key information is transferred from the external command input analyzing unit 50-12 to this file system 50-13. As a result, the desired medical data is searched from the relevant optical disk 22 based upon the key (index) information under control of the file system 50-13 and the file system managing circuit 50-5A.

CLUSTERED DATA RETRIEVING OPERATION

Similarly, when a designation is made of medical data wanted to be outputted, for example, X-ray CT image data of a patient by operating the external command input analyzing unit 50-12, both of the index (key) information about the relevant optical disk 22 containing this medical data, and the positional information (record number) of this medical data within the relevant optical disk 22 are acquired via the file system managing circuit 50-5A, the optical disk cluster managing circuit 50-7 and the optical disk managing circuit 50-6A by the job controller 50-11. Subsequently, the designated optical disk $22_1$, - - - , or $22_n$ is transported from the corresponding slot $24_1$, - - - , or $24_n$ in the optical disk autochanger 50-9 via the buffer controller 50-8 under control of the data transfer controller 50-10. Then, this desired medical data is read out from the designated optical disk and supplied to the output buffer 50-14. From this output buffer 50-14, the read medical data is format-converted in the buffer controller 5-15. Finally, the format-converted desirable medical data is outputted from the medical data output unit 50-17 under control of the output controller 50-16.

ADVANTAGES OF SECOND MEDICAL DATA MANAGING SYSTEM

As previously described in detail, according to the second medical data managing system 200, the cluster condition is newly and additionally employed in connection with the classification conditions of the first medical data managing system 100 before recording a series of medical data on a relevant optical disk, or disks, as the major feature of the second medical data managing system 200. That is to say, the optical disk cluster management table as shown in FIG. 9 is held in the optical disk cluster managing circuit 50-7. Based upon this cluster management table, a proper optical disk $22_1$, - - - , or $22_n$ is selected based on the same recording term (namely, same cluster or group) in conjunction with the classification conditions. As a consequence, the clustered medical data are time-sequentially stored in the relevant optical disks, as illustrated in FIGS. 12A and 12B. Thus, since only one or a limited number of the optical disks 22 are completely filled with the clustered medical data, the respective clustered regions of the remaining optical disks can be used in a rotational wanner. Accordingly, complete filling of all of the optical disks 22 with the clustered medical data at substantially the same time can be avoided.

This implies that such a file system as defined in the table of FIG. 11 can be obtained in accordance with the second medical data managing system 200.

Moreover, although when the plural optical disks are successively filled with the clustered medical data in accordance with a time elapse, the data-filled optical disks are released from the autochanger 20, or replaced by a new optical disk, a frequency of such a replacement can be considerably reduced, as compared with that of the first medical data managing system. Therefore, the higher throughput of the second medical data managing system 200 can be realized than that of the first medical data managing system 100.

While the present invention has been described in detail, the present invention is not limited to the above-described first and second preferred embodiments, but may be changed, modified and substituted without departing from the technical scope and spirit of the present invention. For instance, an opto-magnet disk may be employed instead of an optical disk.

In the second medical data managing system 200, a "temporal term" is defined as the cluster condition. Instead of this term-clustering condition, other conditions may be utilized, e.g., sorts of examinations, patients, modalities, medical departments, date and memory capacities.

Furthermore, the entire cluster structure is subdivided into a plurality of stages, namely, "a hierarchical structure", to which each of the above-defined clustering conditions is allocated, as illustrated in FIG. 13.

What is claimed is:

1. A method for managing medical data comprising the steps of:
    sequentially acquiring a plurality of medical data about a biological body under medical examination;
    classifying said plurality of medical data based upon at least one of medical classification items to obtain a plurality of classified medical data; and
    sequentially storing said plurality of classified medical data into a plurality of data storage mediums in such a manner that said plurality of classified medical data belonging to the same classification item are stored in the same data storage medium.

2. A medical data managing method as claimed in claim 1, further comprising the step of:
    searching desirable medical data from said data storage mediums based upon the classification item covering said desirable medical data.

3. A medical data managing method as claimed in claim 2, further comprising the step of:
    retrieving said searched medical data based upon the classification item covering said searched medical data.

4. A medical data managing method as claimed in claim 1, wherein a temporal term is added to said medical classification items, whereby said plurality of medical data are first classified based upon only said temporal term, and thereafter classified based on said one of the medical classification items.

5. A medical data managing method as claimed in claim 4, further comprising the step of:
    searching desirable medical data from said data storage mediums based upon the classification item covering said desirable medical data.

6. A medical data managing method as claimed in claim 5, further comprising the step of:
    retrieving said searched medical data based upon the classification item covering said searched medical data.

7. A medical data managing method as claimed in claim 4, wherein said temporal term is determined in accordance with a term for medically judging whether a disease of said biological body under medical examination belongs to an acute disease or a chronic disease.

8. A medical data managing method as claimed in claim 1, wherein said medical classification items are selected from a sort of medical examinations, names of patients, sorts of medical departments belonging to patients, and sorts of modalities.

9. A medical data managing method as claimed in claim 4, further comprising the step of:
    subdividing said classified medical data in to a plurality of medical data subdivision groups, said medical data subdivision groups constituting a hierarchical structure.

10. A medical data managing system comprising:
    means for sequentially acquiring a plurality of medical data about a biological body under medical examination;
    means for classifying said plurality of medical data based upon at least one of medical classification items to obtain a plurality of classified medical data; and
    means for sequentially storing said plurality of classified medical data into a plurality of data storage mediums in such a manner that said plurality of classified medical data belonging to the same classification item are stored in the same data storage medium.

11. A medical data managing system as claimed in claim 10, wherein said classifying means further searches desirable medical data from said data storage mediums based upon the classification item covering said desirable medical data.

12. A medical data managing system as claimed in claim 11, wherein said classifying means further retrieves said searched medical data based upon the classification item covering said searched medical data.

13. A medical data managing system as claimed in claim 10, further comprising:
    means for clustering said plurality of medical data acquired from said acquiring means to obtain a plurality of clustered medical data, whereby said clustered medical data are further classified by said classifying means.

14. A medical managing system as claimed in claim 13, wherein said clustering means includes a cluster management table to execute a medical data clustering operation.

15. A medical managing system as claimed in claim 10, wherein said data storage means are optical disks.

16. A medical managing system as claimed in claim 10, wherein said data storage means are opto-magnet disks.

17. A medical data filing system comprising:
    medical data input means for inputting a plurality of medical data about a biological body under medical examination;
    a plurality of storage mediums capable of storing said medical data;
    data information recognizing means for recognizing medical data information attached to said medical data to derive data recognition information;
    storage medium managing means for classifying said plurality of medical data based upon at least one of classification items covering said data recognition information; and
    file system managing means for filing said classified medical data in said storage mediums in such a manner that said classified medical data belonging to the same classification item are filed into the same data storage medium, whereby desirable medical data is searched/retrieved form the data storage mediums based upon the classification item covering the data recognition information of said desirable medical data.

18. A medical data filing system as claimed in claim 17, further comprising:

cluster managing means for first clustering said medical data to obtain a plurality of clustered medical data, whereby said clustered medical data are classified by said storage medium managing means.

19. A medical data filing system as claimed in claim 18, wherein said cluster managing means includes a cluster management table memory containing cluster numbers, storage medium numbers and data acquisition temporal terms.

20. A medical data filing system as claimed in claim 17, wherein said data storage mediums are selected from optical disks and opto-magnet disks.

* * * * *